United States Patent [19]

Hansen

[11] Patent Number: 5,453,081
[45] Date of Patent: Sep. 26, 1995

[54] PULSATOR

[76] Inventor: Craig N. Hansen, 14920 Minnetonka Industrial Rd., Minntonka, Minn. 55345

[21] Appl. No.: 90,234

[22] Filed: Jul. 12, 1993

[51] Int. Cl.$^6$ .................................................. A61H 9/00
[52] U.S. Cl. ......................... 601/150; 601/149; 601/151; 601/48
[58] Field of Search .................... 602/13; 601/48, 601/49, 55, 56, 77, 148, 149, 150, 151, 152, 41, 43, 44, 77; 128/DIG. 20; 5/453, 915

[56] References Cited

U.S. PATENT DOCUMENTS

| | | | |
|---|---|---|---|
| 1,898,652 | 2/1933 | Williams | 601/148 |
| 2,079,694 | 5/1937 | Lovell et al. | |
| 2,354,397 | 7/1944 | Miller. | |
| 2,588,192 | 3/1952 | Akerman et al. | |
| 2,780,222 | 2/1957 | Polzin et al. | |
| 2,869,537 | 1/1959 | Chu. | |
| 3,043,292 | 7/1962 | Mendelson. | |
| 3,310,050 | 3/1967 | Goldfarb. | |
| 3,556,088 | 1/1971 | Leonardini. | |
| 3,672,354 | 6/1972 | Weber. | |
| 3,880,152 | 4/1975 | Nohmura. | |
| 3,993,053 | 11/1976 | Grossan | 601/152 |
| 4,023,566 | 5/1977 | Martinmaas. | |
| 4,066,072 | 1/1978 | Cummins. | |
| 4,093,944 | 6/1978 | Muncheryan. | |
| 4,133,305 | 1/1979 | Steuer. | |
| 4,155,356 | 5/1979 | Venegas | 601/48 |
| 4,232,661 | 11/1980 | Christensen | 601/48 |
| 4,507,816 | 4/1985 | Smith, Jr. | |
| 4,590,925 | 5/1986 | Dillon. | |
| 4,779,615 | 10/1988 | Frazier. | |
| 4,805,612 | 2/1989 | Jensen | 128/204.21 |
| 4,838,263 | 6/1989 | Warwick et al. | |
| 4,840,167 | 6/1989 | Olsson et al. | |
| 4,908,895 | 3/1990 | Walker. | |
| 4,977,889 | 12/1990 | Budd. | |
| 5,020,516 | 6/1991 | Biondi et al. | |
| 5,056,505 | 10/1991 | Warwick et al. | |
| 5,097,821 | 3/1992 | Eakin. | |
| 5,113,852 | 5/1992 | Murtonen | 601/148 |
| 5,233,974 | 8/1993 | Senoue et al. | |
| 5,235,967 | 8/1993 | Arbisi et al. | |

FOREIGN PATENT DOCUMENTS

| | | | |
|---|---|---|---|
| 26799 | 4/1981 | European Pat. Off. | 601/149 |
| 0173499 | 7/1988 | Japan. | |
| 0151396 | 6/1989 | Japan. | |

Primary Examiner—Richard J. Apley
Assistant Examiner—Jeanne M. Clark
Attorney, Agent, or Firm—Richard O. Bartz

[57] ABSTRACT

An apparatus for generating air pressure pulses delivered to a vest or mattress accommodating a person. A diaphragm located within the housing is connected to a wave generator and amplifier operable to vibrate the diaphragm. The vibrating diaphragm produces air pressure pulses which are delivered to the air accommodating receiver to subject the person to repetitive force pulses.

31 Claims, 4 Drawing Sheets

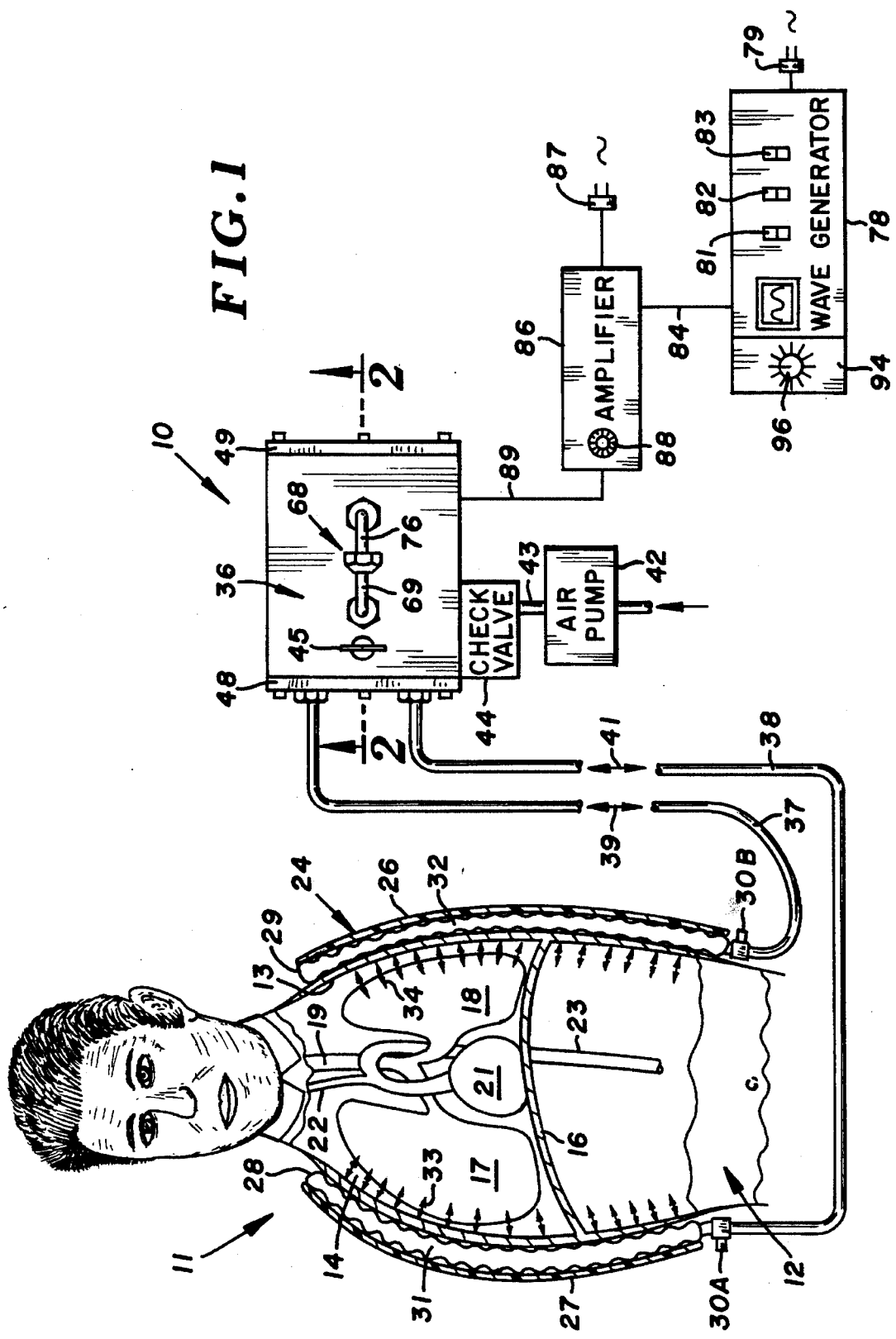

PULSATOR

FIELD OF THE INVENTION

The invention is directed to a medical device used to apply repetitive compression forces to the body of a person to aid blood circulation, loosening and elimination of mucus from the lungs of a person and relieve muscular and nerve tensions.

BACKGROUND OF THE INVENTION

Artificial respiration devices for applying and relieving pressure on the chest of a person have been used to assist in lung breathing functions, and loosening and eliminating mucus from the lungs. Subjecting the person's chest and lungs to pressure pulses or vibrations decreases the viscosity of lung and air passage mucus, thereby enhancing fluid mobility and removal from the lungs. These devices use vests having air accommodating bladders that surround the chests of persons. Mechanical mechanisms, such as solenoid or motor-operated air valves, supply air under pressure to the bladders in regular patterns or pulses. J. D. Ackerman et al in U.S. Pat. No. 2,588,192, discloses an artificial respiration apparatus having a chest vest supplied with air under pressure with an air pump. Solenoid-operated valves control the flow of air into and out of the vest in a controlled manner to pulsate the vest, thereby subjecting the person's chest to repeated pressure pulses. W. J. Warwick and L. G. Hansen, in U.S. Pat. No. 5,056,505, disclose a chest compression apparatus having a chest vest surrounding a person's chest. A motor-driven rotary valve allows air to flow into the vest and vent air therefrom to apply pressurized pulses to the person's chest.

R. S. Dillion in U.S. Pat. No. 4,590,925 uses an inflatable enclosure to cover a portion of a person's extremity, such as an arm or leg. The enclosure is connected to a fluid control and pulse monitor operable to selectively apply and remove pressure on the person's extremity. R. L. Weber in U.S. Pat. No. 3,672,354 discloses a rest inducing device having an air mattress supplied with air in pulses from an air pump at the frequency of the person's heartbeat.

SUMMARY OF THE INVENTION

The invention is directed an apparatus for applying pressure pulses to a portion of a person to assist body functions including blood flow, muscle and nerve relaxation and loosening and eliminating mucus from the lungs. The apparatus operates with air under pressure at a selected frequency and force to apply repetitive pressure pulses to a person. In use, the apparatus has a relatively low noise output and can be under the control of the user as well as an attendant.

The apparatus generates repetitive air pressure pulses which are delivered to a receiver, such as a vest, jacket or mattress adapted to accommodate a portion of the body of a person to apply pressure pulses to said person. A housing having an enclosed chamber accommodates a diaphragm which divides the chamber into two separate portions. Air under pressure is supplied with a pump to the chamber to pressurize the apparatus, as well as the receiver. A coil connected to the diaphragm is operable to vibrate the diaphragm to pulsate the air in the chamber. A wave generator generates a wave signal which energizes the coil. An amplifier is used to amplify or provide a gain signal to the coil to control the output of the coil. The wave generator has controls to adjust the frequency of the wave signal as well as the wave form to provide the apparatus with versatility of the type of pressure pulse that is to be applied to the person.

In one embodiment of the apparatus, repetitive pressure pulses are applied to a portion of a person with the use of flexible air accommodating structure that engages a portion of the person to be subjected to repetitive pressure pulses. A pulsator operates to produce air pressure pulses. A hose connects the pulsator with the air accommodating structure so that the air pressure pulses repetitively move the air accommodating structure to apply pressure pulses to a portion of the person. The pulsator has a housing, including an enclosed chamber, which accommodates a diaphragm. The diaphragm divides the chamber into two portions. Air is supplied with a pump to the chamber for subjecting the chamber as well as the flexible air accommodating structure with air under pressure. A coil operates to vibrate the diaphragm to pulsate the air in the chamber. The hose being connected to the housing is open to the chamber so that the air in the air accommodating structure is pulsed, which in turn subjects a portion of the person to repetitive pressure pulses. A wave generator operates to produce a wave signal which drives the coil thereby vibrating the diaphragm to pulsate the air in the chamber and air accommodating structure. An amplifier connected to the wave generator operates to amplify the wave signal to control the output of the coil thereby controlling the vibration intensity of the diaphragm. The amplifier includes a control that is used to adjust the gain of the output signal of the amplifier thereby adjusting the output power of the coil intensity of the vibrations of the diaphragm. The intensity of the vibrations of the diaphragm alter the air pressure differential of the air in the chamber and air accommodating structure thereby controlling the force of the pressure pulses that are subjected to the person.

DESCRIPTION OF DRAWING

FIG. 1 is a diagrammatic view of the medical device of the invention for applying repetitive force pulses to the body of a human;

DESCRIPTION OF PREFERRED EMBODIMENTS

Figure 3:
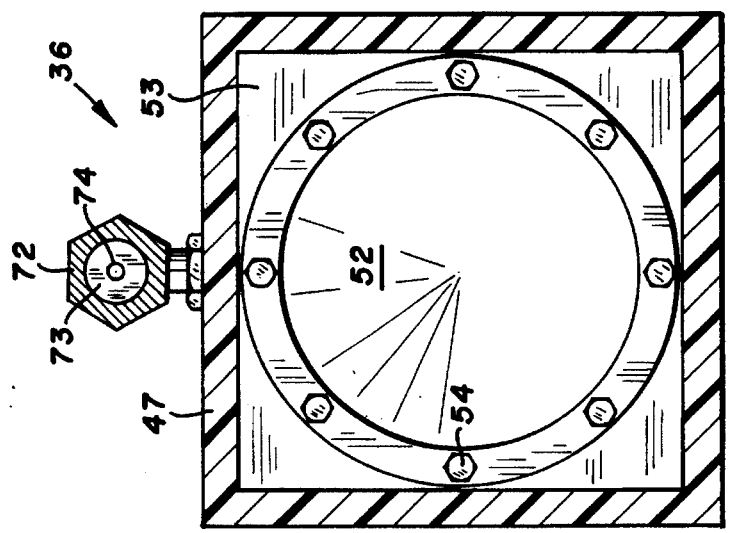
FIG. 3 is a sectional view taken along the line 3—3 of FIG. 2.

Referring to FIG. 1, there is shown a medical device, indicated generally at 10, useable to provide repetitive pressure or force pulses to the body of a human to alleviate mucus and fluids in the lungs, to aid in blood circulation and relieve muscular tensions. Person 11 has a body 12 including thorax wall 13 surrounding a chest cavity 14. The lower part of chest cavity 14 has transverse diaphragm 16 located below lungs 17 and 18. Trachea 19 leads from lungs 17 and 18 to the mouth of the person. Chest cavity 14 also accommodates the heart 21, which pumps blood under pressure through systematic aorta 22 and descending artery 23.

A vest, indicated generally at 24, is positioned about body 12. Vest 24 comprises outer jackets 26 and 27 placed about the front and back of thorax wall 13. Jackets 26 and 27 surround flexible air bags or cores 28 and 29 having internal chambers 31 and 32. The material of air bags 28 and 29 is flexible, with the inner side of each air bag located adjacent thorax wall 13. Jackets 26 and 27 are made of rigid shells or non-elastic material that has sufficient rigidity to direct the pulsating forces indicated by arrows 33 and 34, caused by changes of air pressure in air bags 28 and 29 to be directed inwardly into the body toward lungs 17 and 18. The body 12 has reaction forces to the pressure pulses which further enhance the advantageous functions of the device. Medical device 10 can be connected to and adapted to fit around a human leg, thigh or arm to apply repetitive forces to the leg, thigh or arm. An example of the repetitive forces that aids in blood circulation and massages is disclosed by R. S. Dillion in U.S. Pat. No. 4,590,925.

Figure 2:
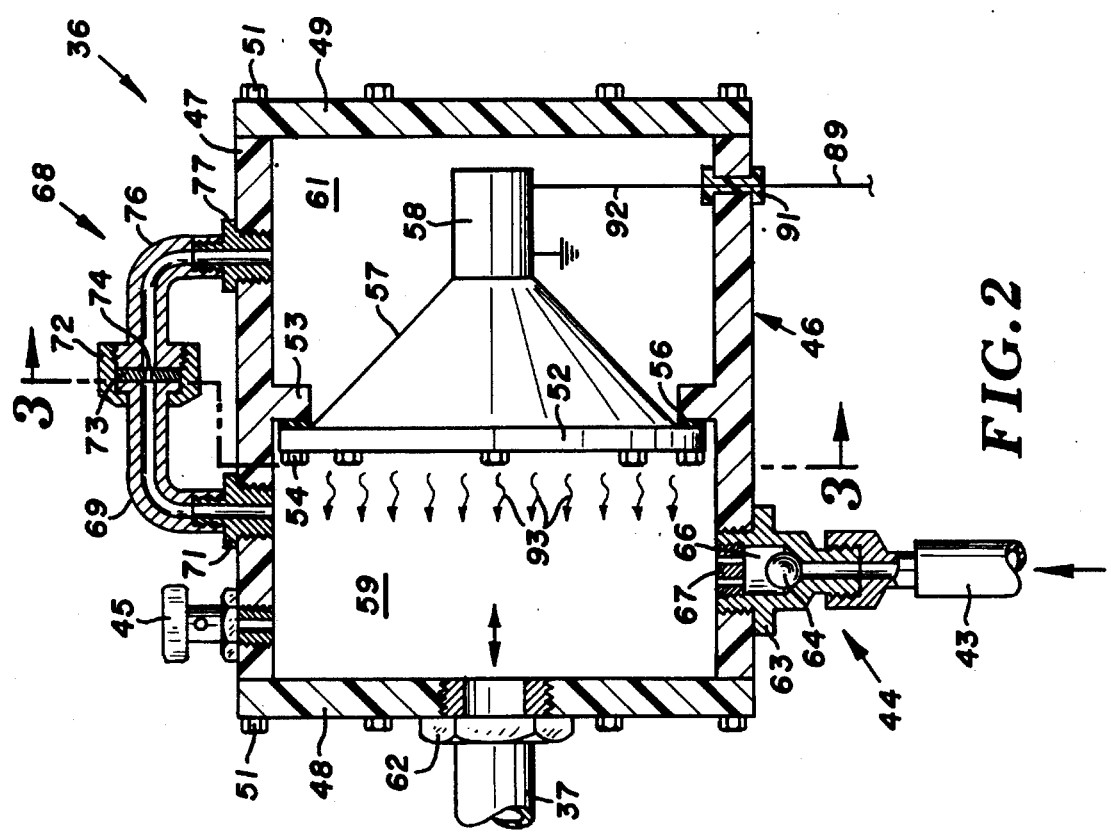
FIG. 2 is an enlarged sectional view taken along the line 2—2 of FIG. 1.

Air bags 28 and 29 are connected to a pulsator, indicated generally at 36, with air lines or hoses 37 and 38. Hoses 37 and 38 are tubular members of flexible non-electrical conductive material so that the body of the person is not subject electrical energy from pulsator 36, amplifier 86 or wave generator 78. Hoses 37 and 38 carry pulses of air under pressure indicated by arrows 39 and 41 to chambers 31 and 32 of air bags 28 and 29. Pulsator 36 is connected to air pump 42 with hose 43. Air pump 42 operates to initially pressurize the air in pulsator 36, lines 37 and 38 and chambers 31 and 32 to a selected pressure, such as one psi. Air pressure relief valves 30A and 30B connected to lines 37 and 38 and air bags 28 and 29, prevent air flow out and adverse pressure on body 12. An example of an air pressure relief valve is disclosed in U.S. Pat. No. 4,908,895. As seen in FIG. 2, line 43 is connected to check valve 44 operable to allow air into pulsator 36 and prevent the escape of air from pulsator 36 and air bags 28 and 29.

Pulsator 36, as seen in FIGS. 2 and 3, has housing 46 comprising side wall 47 connected to end walls 48 and 49 with bolts 51. Diaphragm 52 bisects the mid-portion of housing 46. The outer edge portion of diaphragm 52 is mounted on an inwardly directed rib 53 with a plurality of bolts 54. Cushion or vibration insulation material 56 is interposed between diaphragm 52 and rib 53. Diaphragm 52 is connected to conical shell 57 supporting an electric coil 58 operable to vibrate diaphragm 52. Diaphragm 52 bisects the internal space of housing 46 into first chamber 59 and second chamber 61.

Hose 37 is secured to end wall 48 with tubular connector 62, which allows the air in chamber 59 to flow through hose 37 to air chamber 32 of air bag 29. A second hose 38 is also connected to end wall 48 and carries air under pressure to chamber 31 of air bag 28. A single tube or hose can be used to connect air bags 28 and 29 with pulsator 36.

Returning to FIG. 2, check valve 44 has connector or housing 63 having chamber 66 accommodating check ball 64. The inner end of chamber 66 is closed with perforated plug 67 to allow air to flow through the check valve into chamber 59. Ball 64, when lowered on its seat, blocks the reverse flow of air from chamber 59 back into hose 43 leading to pump 42. Other types of check valves can be used to maintain the air pressure within pulsator 36 and air bags 28 and 29. A manually operated open and close valve 45 mounted on wall 47 is used to vent air from chamber 59 and relieve the air pressure from air bags 28 and 29. Hoses 37 and 38 can also be uncoupled from end wall 48 to allow air to escape to the atmosphere.

Pulsator 36 has an air pressure balance device, indicated generally at 68, to balance the air pressure between chambers 59 and 61. Device 68 has a first elbow or tube 69 connected to a nipple connector 71, mounted on side wall 47 and open to chamber 59. Elbow 69 has female end 72 that accommodates disk 73 having a small central hole 74 that restricts the flow of air between chambers 59 and 61. Second elbow 76, joined to nipple connector 77, mounted on side wall 47, is open to chamber 61. Elbow 76 is connected to female end 72 and thereby provides a continuous restricted passage for air between chambers 59 and 61.

Returning to FIG. 1, pulsator 36 is driven with wave generator 78 connected to an AC electrical power source with plug 79. Wave generator 78 has a plurality of switches 81, 82 and 83, operable to select a desired wave form, such as a square wave, a sinusoidal wave, or a spike wave, as well as other wave forms. Generator 78 has a wave frequency control 94 having adjusting dial 96. Operator or person 11 can manually use dial 96 to adjust the frequency of the signal sent to amplifier 86. The operator or patient can select the wave form and frequency of the signal with generator 78. Amplifier 86 is used to control the power of the signal sent to coil 58 thereby controlling the vibrations and air pumping characteristics of diaphragm 52. Line 84 connects wave generator 78 to amplifier 86, powered by AC power connected thereto with AC power plug 87. Wave generator 78 and amplifier 86 can be located within a casing that includes pulsator 36. Amplifier 86 has a control 88 operable to adjust the amplification or gain of a power signal carried by line 89 to coil 58, thereby controlling the output power of coil 58 and amplitude of the vibrations of diaphragm 52. The vibrations of diaphragm 52 cause air pressure changes or flexion of pressure pulses which are transmitted by the air in the system to air bags 28 and 29. The frequency of the power signal is determined by the operation of frequency control 94. Line 89 is plugged into electrical connector 91 that is connected with line 92 to coil 58. Vibrating diaphragm 52 generates air pressure differences or force pulses indicated by arrows 93 in FIG. 2 in the air in chamber 59. These pulses are a ripple pressure wave which increase and decrease the pressure of the air in chamber 59 and air cores 28 and 29 in an air pressure change range of 0.25 psi. Other differences in air pressure can be generated by pulsator 36.

In use, vest 24 is placed about body 12 of human 11 and covers the torso from the thoracic wall 13 around lungs 17 and 18. Air pump 42 is operated to inflate air bags 28 and 29 to a selected pressure, such as 1 psi. A pressure relief valve 30A, 30B is useable to prevent excessive air pressure in air bags 28 and 29. When the selected pressure is obtained, air pump 42 is turned OFF, as check valve 44 maintains the air pressure in air bags 28 and 29, as well as pulsator 36. Wave generator 78 establishes the wave signal, which is amplified by amplifier 86 to drive coil 58. Operation of coil 58 causes diaphragm 52 to vibrate thereby establishing the ripple pressure wave in air chamber 59. The result is that air bags 28 and 29 transmit controlled air pressure pulses as indicated by arrows 33 and 34 to thoracic wall 13 to facilitate the loosening and elimination of mucus from the lungs of a person, aid blood circulation and relieve muscular and nerve tensions. Valve 45 is opened to vent air from the system which deflates air bags 28 and 29. Vest 24 can then be removed from body 12.

Figure 4:
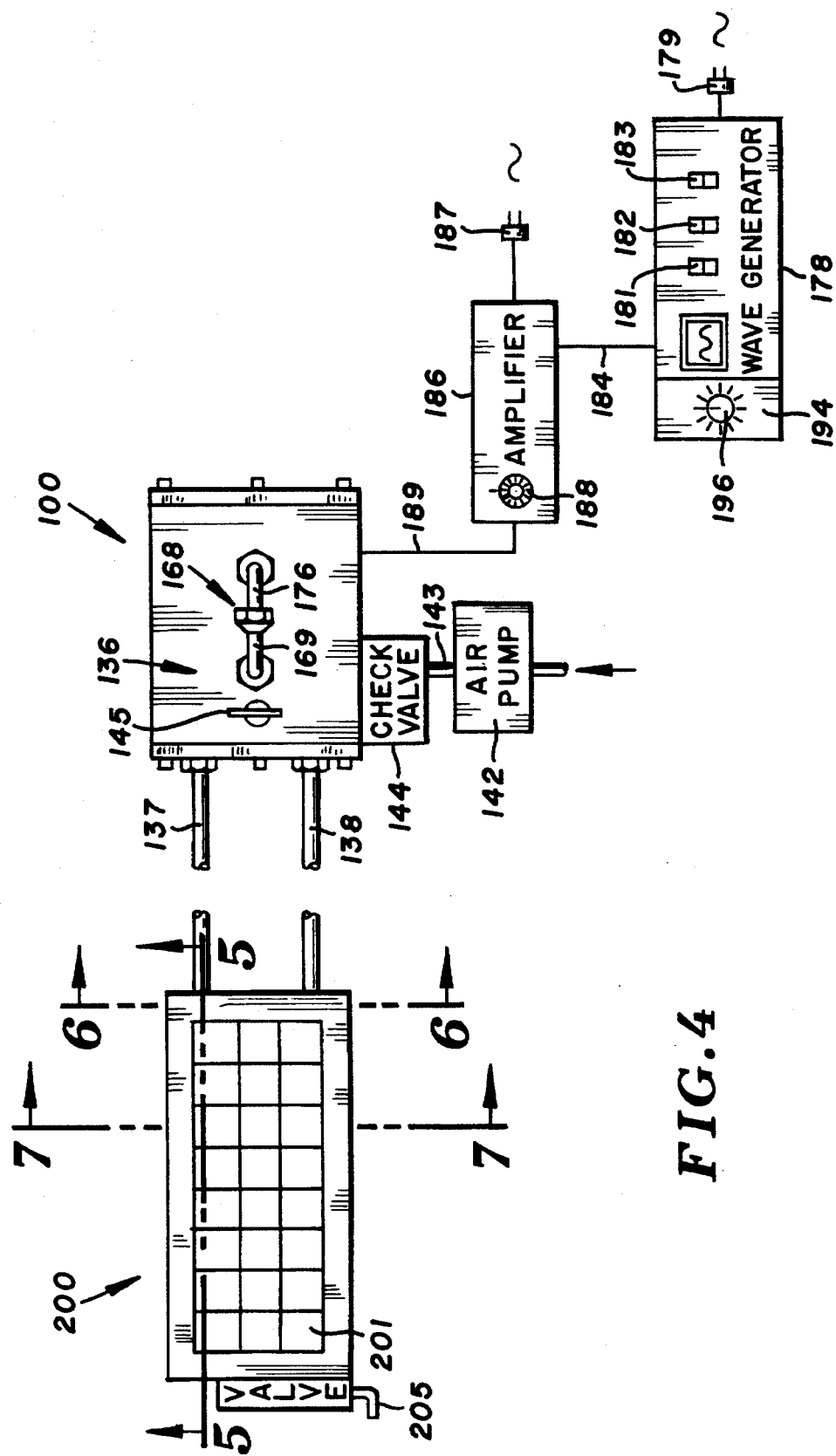
FIG. 4 is a diagrammatic view of a modification of the medical device of the invention applying repetitive force to an air mattress for supporting a human body.

Referring to FIG. 4, there is shown a diagrammatic illustration of a modification of the medical device indicated generally at 100, useable to provide repetitive pressure or force pulses to an air mattress or core, indicated generally at 200. Mattress 200 is used to accommodate one or more persons which are subjected to the repetitive force pulses to alleviate muscle and nerve tensions and facilitate blood circulation. Medical device 100 has the same operating structure as the medical device shown in FIGS. 1–3. The corresponding parts have the same reference numbers with the prefix "1". Pulsator 136 is electrically coupled to amplifier 186, which receives a signal from wave generator 178. Wave generator 178 has a wave frequency adjusting control 194 for controlling the frequency of the output signal that is supplied to amplifier 186. The frequency of the pulses, as well as the amplitude of the pulses, is individually controlled to allow pulsator 136 to deliver controlled pulsating air pressure forces to mattress 200.

Figure 5:
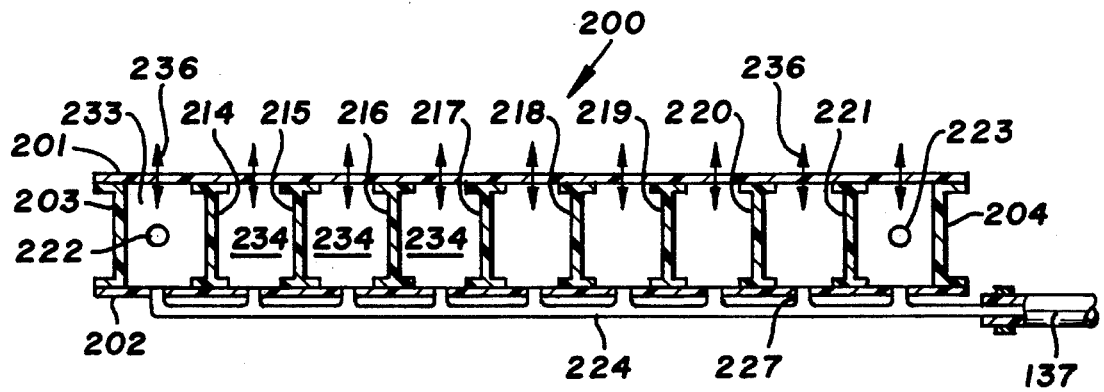
FIG. 5 is an enlarged sectional view taken along the line 5—5 of FIG. 4.
Figure 6:
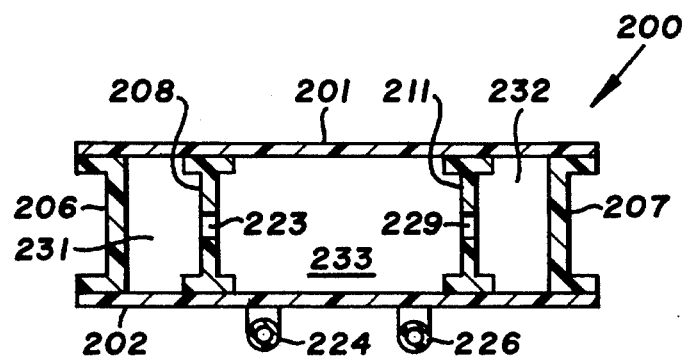
FIG. 6 is an enlarged sectional view taken along the line 6—6 of FIG. 4.
Figure 7:
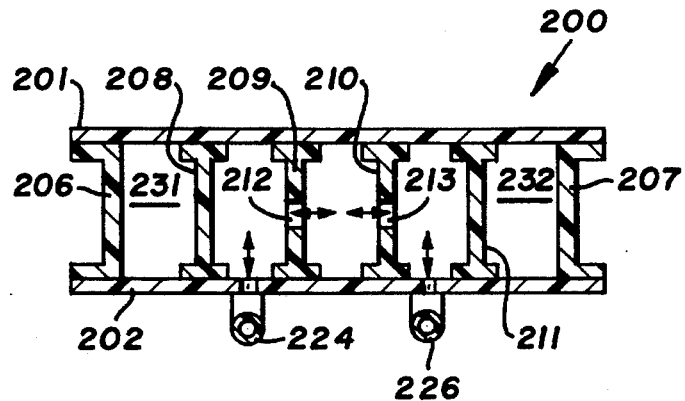
FIG. 7 is an enlarged sectional view taken along the line 7—7 of FIG. 4.

As shown in FIGS. 5–7, mattress 200 is an air inflatable core having generally rectangular top wall 201 located above bottom wall 202. Side walls 203 and 204, and end walls 206 and 207 are secured to the outer peripheral edges of the top and bottom walls to complete the air mattress. A plurality of longitudinal baffles 208, 209, 210 and 211 extend longitudinally in the internal portion of the air mattress between the top and bottom walls. Baffles 208–211 are secured to the inner surfaces of top and bottom walls 201 and 202. Baffles 208–211 extend generally parallel to side walls 203 and 204. As seen in FIG. 7, interior baffles 209 and 210 have a plurality of holes 212 and 213 to allow air to flow into the central chamber of the air mattress. An air pressure relief check valve 205 is secured to end wall 203 to limit the pressure of the air in mattress 200 to about 1 psi thereby minimizing blow-out of the mattress.

As seen in FIG. 5, a plurality of transverse baffles 214, 215, 216, 217, 218, 219, 220 and 221 separate the interior portion of the mattress into generally cubic chambers 234. As seen in FIG. 4, the mattress has 24 cubic chambers. The end portions of the mattress has holes 222, 223 and 229 in longitudinal baffles 208 and 211 to allow air to flow into side chambers 231 and 232. The air under pressure is delivered to chambers 231 and 232, as well as cubic chambers 234. A pair of longitudinal tubes 224 and 226 are connected with separate nipples or tubular connectors 227 to bottom wall 202 to allow air to flow into the chambers. Other structures can be used to supply air to each of the chambers of air mattress 200 to subject the chambers to variations in air pressure so that top wall 201 will pulsate or move up and down, as indicated by arrows 236 in FIG. 5.

In use, mattress 200 is placed in a horizontal position on a support or bed. Air pump 142 is operated to inflate mattress 200 with air and maintain the pressure of the air at a selected level, such as 1 psi. Pressure relief valve 205 prevents over inflation of mattress 200. When the selected air pressure in mattress 200 is attained, pump 142 is turned OFF. The person can then recline on mattress 200. Pulsator 136 operates to deliver air pressure pulses to mattress 200 which cause top wall 201 to move up and down. Each cell of mattress 200 is subjected to air pressure pulses so as to provide a pattern of spaced pressure forces on the body of the person which tends to aid blood circulation and relieve muscular and nerve tensions. The frequency and power of the pressure pulses can be altered by adjusting the controls for the wave generator and amplifier.

While there have been shown and described several embodiments of the device of the invention and uses thereof, it is understood that changes in structures, components and arrangement of structures can be made by one skilled in the art without departing from the invention. The invention is defined in the following claims.

I claim:

1. In combination, an apparatus for generating repetitive air pressure pulses and an air accommodating structure coupled to the apparatus for subjecting a portion of a person to repetitive pressure pulses to assist body functions comprising: means for accommodating air under pressure including at least one flexible member adapted to engage a portion of a person and an enclosed first internal chamber located within the flexible member, housing means having an enclosed second internal chamber, diaphragm means located within said second internal chamber dividing the second internal chamber into a first chamber means and a second chamber means, for supplying air under pressure to at least one of said chamber means, and first internal chamber, check valve means for maintaining the pressure of the air within said one of the chamber means and first internal chamber when the means for supplying air under pressure is not operating, coil means for vibrating the diaphragm means to pulsate the air in the first chamber means, and first internal chamber thereby moving said flexible member to apply repetitive pressure pulses to the person, means for carrying air under pressure including a passage open to the one of the chamber means and first internal chamber for carrying air under pressure to the first internal chamber whereby the flexible member is subjected to air pressure pulses, wave generator means for generating a wave signal, and means for connecting the wave generator means to the coil means whereby the signal from the wave generator means energizes the coil means which vibrates the diaphragm means to pulsate the air in said first chamber means and first internal chamber.

2. The combination of claim 1 including: amplifier means connected to the wave generator means for amplifying the wave signal to control the output power of the coil means thereby controlling the vibrations intensity of the diaphragm means.

3. The combination of claim 2 wherein: said amplifier means includes control means to adjust the gain of the output signal of the amplifier means thereby adjusting the output power of the coil means.

4. The combination of claim 1 wherein: the wave generator means includes means to adjust the frequency of the wave signal generated by the wave generator means.

5. The combination of claim 1 wherein: the wave generator means includes means to change the wave form of the wave signal generated by the wave generator means.

6. The combination of claim 1 wherein: the wave generator means includes first means to change the wave form of the wave signal generated by the wave generator means, and second means to adjust the frequency of the wave signal generated by the wave generator means.

7. The combination of claim 1 including: means for allowing air to flow from the first chamber means to the second chamber means to balance the air pressure between said first and second chamber means.

8. The apparatus of claim 7 wherein: the means to balance the air pressure between said first and second chamber means includes tubular means having an air passage connecting said first and second chamber means, and means for restricting the flow of air between said first and second chamber means including a hole located in said air passage to restrict the flow of air between said first and second chamber means.

9. The combination of claim 1 including: means mounting the diaphragm means on said housing means to locate the diaphragm means within said second chamber.

10. The combination of claim 1 including: shell means located within the second chamber connecting the diaphragm means with the coil means, and means mounting the shell means on said housing means to locate the diaphragm means, shell means and coil means within said second chamber means.

11. The combination of claim 1 wherein: the means having at least one flexible member comprises a non-elastic member and an air bag having said first internal chamber and flexible member located adjacent said non-elastic member whereby the flexible member directs pressure pulses toward the portion of the person located adjacent the flexible member.

12. An apparatus for providing repetitive pressure pulses to a portion of a person to assist body functions comprising: means for accommodating air under pressure including at least one flexible member adapted to engage a portion of a person and an enclosed first internal chamber located within the flexible member that is to be subjected to repetitive pressure pulses, a pulsator operable to produce air pressure pulses, hose means connecting the pulsator with the flexible means, said hose means having an air passage open to the first chamber whereby the air pressure pulses repetitively move the flexible means which applies pressure pulses to the portion of a person, said pulsator having housing means including an enclosed second chamber, diaphragm means located within said second chamber dividing the second chamber into a first chamber means and a second chamber means, means for supplying air to the first chamber means, check valve means for maintaining the pressure of the air within said first chamber means and said first chamber when the means for supplying air under pressure is not operating, coil means for vibrating the diaphragm means to pulsate the air in the first chamber means, said hose means being connected to the housing means and open to the first chamber means whereby the air in said first chamber is pulsated, which in turn subjects the portion of a person to repetitive pressure pulses, wave generator means for generating a wave signal, and means connecting the wave generator means to the coil means whereby the signal from the wave generator means energizes the coil means, which vibrates the diaphragm means to pulsate the air in said first chamber means and first chamber.

13. The apparatus of claim 12 including: amplifier means connected to the wave generator means for amplifying the wave signal to control the output power of the coil means thereby controlling the vibrations intensity of the diaphragm means and the force of the pressure pulses applied to the person.

14. The apparatus of claim 13 wherein: said amplifier means includes control means to adjust the gain of the output signal of the amplifier means thereby adjusting the output power of the coil means.

15. The apparatus of claim 12 wherein: the wave generator means includes means to adjust the frequency of the wave signal generated by the wave generator means.

16. The apparatus of claim 12 wherein: the wave generator means includes means to change the wave form of the wave signal generated by the wave generator means.

17. The apparatus of claim 12 wherein: the wave generator means includes first means to change the wave form of the wave signal generated by the wave generator means, and second means to adjust the frequency of the wave signal generated by the wave generator means.

18. The apparatus of claim 12 including: means for allowing air to flow from the first chamber means to the second chamber means to balance the air pressure between said first and second chamber means.

19. The apparatus of claim 18 wherein: the means to balance the air pressure between said first and second chamber means includes tubular means having an air passage connecting said first and second chamber means, and means for restricting the flow of air between said first and second chamber means including a hole located in said air passage to restrict the flow of air between said first and second chambers means.

20. The apparatus of claim 12 including: means mounting the diaphragm means on said housing means to locate the diaphragm means within said second chamber.

21. The apparatus of claim 12 including: shell means located within the second chamber connecting the diaphragm means with the coil means, and means mounting the shell means on said housing means to locate the diaphragm means, shell means and coil means within said second chamber means.

22. The apparatus of claim 12 wherein: the means having an enclosed first chamber and flexible means comprises a non-elastic member and an air bag having said first internal chamber and flexible means located adjacent the non-elastic member whereby the flexible means directs pressure pulses toward the portion of the person located adjacent the flexible means.

23. An apparatus for providing repetitive pressure to a portion of a person to assist body functions comprising: means for accommodating air under pressure including at least one flexible member adapted to engage a portion of a person and an enclosed first internal chamber located within the flexible member that is to be subjected to repetitive pressure pulses, a pulsator operable to produce air pressure pulses, means having an air passage connecting the pulsator with the first chamber whereby the air pressure pulses repetitively move the flexible means which applies pressure pulses to said portion of a person, said pulsator having housing means including an enclosed second chamber, diaphragm means located within said second chamber, means for supplying air under pressure to the second chamber and first chamber, means for vibrating the diaphragm means to pulsate the air in the first and second chambers, said means having an air passage being connected to the housing means and open to the second chamber whereby the air in said first chamber is pulsated, which in turn subjects the portion of a person to repetitive pressure pulses, wave generator means for generating a wave signal, and means connecting the wave generator means to the means for vibrating the diaphragm means whereby the signal from the wave generator means energizes the means to pulsate the air in said first chamber and second chamber.

24. The apparatus of claim 23 including: amplifier means connected to the wave generator means for amplifying the wave signal to control the output of the means for vibrating the diaphragm means thereby controlling the vibration intensity of the diaphragm means and the force of the pressure pulses applied to the person.

25. The apparatus of claim 24 wherein: said amplifier means includes control means to adjust the gain of the output signal of the amplifier means thereby adjusting the output power of the means for vibrating the diaphragm means.

26. The apparatus of claim 23 wherein: the wave generator means includes means to adjust the frequency of the wave signal generated by the wave generator means.

27. The apparatus of claim 23 wherein: the wave generator means includes means to change the wave form of the wave signal generated by the wave generator means.

28. The apparatus of claim 23 wherein: the wave generator means includes first means to change the wave form of the wave signal generated by the wave generator means, and second means to adjust the frequency of the wave signal generated by the wave generator means.

29. The apparatus of claim 23 including: means mounting the diaphragm means on said housing means to locate the diaphragm means within said second chamber.

30. The apparatus of claim 23 including: shell means located within the second chamber connecting the diaphragm means with the means for vibrating the diaphragm means, and means mounting the shell means on said housing means to locate the diaphragm means, shell means and means for vibrating the diaphragm means within said second chamber.

31. The apparatus of claim 23 including: check valve means connected to the means for supplying air under pressure to said second chamber for preventing escape of air from said first and second chambers.

* * * * *